United States Patent
Boldingh et al.

(10) Patent No.: US 8,481,795 B2
(45) Date of Patent: Jul. 9, 2013

(54) PROCESSES FOR TRANSALKYLATING AROMATIC HYDROCARBONS AND CONVERTING OLEFINS

(75) Inventors: Edwin P. Boldingh, Arlington Heights, IL (US); Robert J. L. Noe, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 111 days.

(21) Appl. No.: 13/234,673

(22) Filed: Sep. 16, 2011

(65) Prior Publication Data

US 2012/0083638 A1  Apr. 5, 2012

Related U.S. Application Data

(60) Provisional application No. 61/388,006, filed on Sep. 30, 2010.

(51) Int. Cl.
*C07C 6/12* (2006.01)
*C07C 5/03* (2006.01)

(52) U.S. Cl.
USPC ............................ 585/475; 585/800; 585/258

(58) Field of Classification Search
USPC .......................................... 585/475, 258, 800
See application file for complete search history.

(56) References Cited

U.S. PATENT DOCUMENTS

| | | | |
|---|---|---|---|
| 6,500,996 B1 | 12/2002 | Brown et al. | |
| 2009/0036724 A1* | 2/2009 | Negiz et al. | 585/470 |

* cited by examiner

*Primary Examiner* — Thuan D Dang
(74) *Attorney, Agent, or Firm* — Mark R Willis

(57) ABSTRACT

A process for aromatic transalkylation and olefin reduction of a feed stream is disclosed. Transalkylation conditions produce xylenes and reduced olefins in the feed. The process may be used in a xylene production facility to minimize or avoid the necessity of feedstock pretreatment such as hydrotreating, hydrogenation, or treating with clay and/or molecular sieves.

19 Claims, No Drawings

PROCESSES FOR TRANSALKYLATING AROMATIC HYDROCARBONS AND CONVERTING OLEFINS

CROSS-REFERENCE TO RELATED APPLICATION

This application claims the benefit of U.S. Provisional Application No. 61/388,006 filed Sep. 30, 2010.

FIELD OF THE INVENTION

This invention pertains to aromatic transalkylation processes. In particular, the invention relates to processes which transalkylate feed aromatics to produce xylene and convert feed olefins.

DESCRIPTION OF RELATED ART

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production. The distribution of xylene isomers from catalytic reforming and other sources generally does not match that of the sought isomers for chemical intermediates and thus the producer converts feed stocks to generate more of the sought isomers.

Transalkylation processes are known to convert various aromatic hydrocarbons to xylenes. Transalkylation may be combined with other processes such as isomerization, and xylene isomer separation in various configurations to produce one or more specific isomers of xylene. A prior art aromatics complex flow scheme has been disclosed by Meyers in part 2 of the HANDBOOK OF PETROLEUM REFINING PROCESSES, Second Edition, 1997, published by McGraw-Hill.

The feed to an aromatic transalkylation process may be obtained from a variety of sources including the catalytic reforming of naphtha fractions, pyrolysis of hydrocarbons, and other processes in an aromatic complex. In addition to producing desired aromatic feed components, these processes produce other chemical compounds including olefins. Olefins have been generally considered undesirable feed impurities and have been limited to a maximum contaminant level. Various pretreatment steps such as clay treating, hydrotreating, and hydrogenation have been used to remove olefins from the feed before the transalkylation process. US 2009/0036724 A1 discloses catalysts that produce xylenes and remove olefins in a transalkylation process.

There remains a need in the art for alternate transalkylation processes capable of producing xylenes and removing olefins.

SUMMARY OF THE INVENTION

Transalkylation processes according to the invention may be part of a xylene production complex, another arrangement of process units, or a stand alone processing unit. In general, the feed to the transalkylation zone comprises aromatic hydrocarbon and olefin compounds and the transalkylation zone produces xylenes and reduces the olefin content of the feed. The invention may be used to minimize or avoid the necessity of feedstock pretreatment such as hydrotreating, hydrogenation, or treating with clay and/or molecular sieves.

In an embodiment, the invention is a process for transalkylating aromatic hydrocarbons and removing olefins from a feed having a Bromine Index of more than 50 comprising introducing a feed comprising the olefin and aromatic hydrocarbon compounds to a transalkylation zone; contacting the feed with a catalyst in the transalkylation zone under transalkylation conditions; and producing a reaction product stream having an increased concentration of xylenes relative to the feed and at least 60% lower olefins as determined by Bromine Index relative to the feed. The catalyst comprises an aluminosilicate zeolite component having an MOR framework type, an MFI molecular sieve component having a $Si/Al_2$ molar ratio of less than 80, an inorganic oxide binder, and a metal component comprising a metal consisting essentially of molybdenum.

DETAILED DESCRIPTION

The aromatic hydrocarbons to be transalkylated by processes of the invention include alkylaromatic hydrocarbons of the general formula $C_6H_{(6-n)}R_n$, where n is an integer from 0 to 5 and R is $CH_3$, $C_2H_5$, $C_3H_7$, or $C_4H_9$, in any combination. Non-limiting examples include: benzene, toluene, ethylbenzene, ethyltoluenes, propylbenzenes, tetramethylbenzenes, ethyl-dimethylbenzenes, diethylbenzenes, methylethylbenzenes, methylpropylbenzenes, ethylpropylbenzenes, triethylbenzenes, trimethylbenzenes, di-isopropylbenzenes, and mixtures thereof. In an embodiment, the feed stream includes up to about 35 mass percent of $C_8$ aromatics. In another embodiment, the feed stream includes up to about 30 mass percent of $C_8$ aromatics; the $C_8$ aromatic content of the feed stream may range from about 5 to about 25 mass percent and the $C_8$ aromatic content of the feed stream may be less than about 5 mass percent.

As used herein, the term "transalkylation" encompasses transalkylation between and among alkyl aromatics, between benzene and alkyl aromatics, and it includes dealkylation and disproportionation, e.g., of toluene to benzene and xylene. The aromatic hydrocarbons also may comprise naphthalene and other $C_{10}$ and $C_{11}$ aromatics. Herein, hydrocarbon molecules may be abbreviated $C_1$, $C_2$, $C_3$, . . . $C_n$, where "n" represents the number of carbon atoms in the hydrocarbon molecule. Such abbreviations followed by a "+" is used to denote that number of carbon atoms or more per molecule, and a "−" is used to denote that number of carbon atoms or less per molecule.

Polycyclic aromatics having from 2 to 4 rings are permitted in the feed stream of the present invention. Non-limiting examples include: indanes, naphthalenes, tetralins, decalins, biphenyls, diphenyls and fluorenes. Indane is meant to define a nine carbon atom aromatic species with one ring of six carbon atoms and one ring of five carbon atoms wherein two carbon atoms are shared. Naphthalene is meant to define a ten carbon atom aromatic species with two rings of six carbon atoms wherein two carbon atoms are shared.

The aromatic hydrocarbons to be transalkylated may be introduced to the transalkylation zone in one or more feed streams. As used herein, the term "zone" can refer to one or more equipment items and/or one or more sub-zones. Equipment items may include, for example, one or more vessels, heaters, separators, exchangers, conduits, pumps, compressors, and controllers. Additionally, an equipment item can further include one or more zones or sub-zones. In embodiments having multiple feed streams, the feed streams may be introduced separately to the transalkylation zone, or two or more of the feed streams may be combined in any manner prior to passing them into the transalkylation zone.

The feed streams may be derived from one or more sources including, without limitation, catalytic reforming, pyrolysis of naphtha, distillates or other hydrocarbons to yield light olefins and heavier aromatics-rich byproducts, and catalytic or thermal cracking of heavy oils to yield products in the gasoline range. Products from pyrolysis or other cracking operations generally will be hydrotreated according to processes well known in the industry before being charged to the transalkylation zone in order to remove sulfur and other compounds which would affect product quality. Light cycle oil also may be beneficially hydrocracked to yield lighter components which can be reformed catalytically to yield the aromatics-rich feed stream. If the feed stream is catalytic reformate, the reformer preferably is operated at high severity for high aromatics yield with a low concentration of non-aromatics in the product. In an embodiment, reformate and other feed streams containing olefins may be processed in the transalkylation zone without pretreatment to remove olefins.

A feed stream can include a substantially pure alkylaromatic hydrocarbon of from about 6 to about 15 carbon atoms, a mixture of such alkylaromatic hydrocarbons, or a hydrocarbon fraction rich in said alkylaromatics. A feed stream also may contain lesser concentrations of non-aromatics such as pentanes, hexanes, heptanes and heavier paraffins along with paraffins along with methylcyclopentane, cyclohexane and heavier naphthenes; pentanes and lighter paraffins generally will have been removed before processing. The combined transalkylation feed preferably contains no more than about 10 wt % non-aromatics.

In an embodiment, at least two feed streams are introduced to the transalkylation zone, a light feed stream and a heavy feed stream. The light aromatic feed stream may comprise at least one of benzene and toluene. Preferred components of the heavy aromatic feed are $C_9+$ aromatics, thereby effecting transalkylation of toluene and $C_9+$ aromatics to yield additional xylenes. Benzene may also be transalkylated to yield additional toluene. Indane may be present in the heavy aromatics feed stream although it is not a desirable component to effect high yields of xylenes in the transalkylation zone effluent. $C_{10}+$ aromatics also may be present, preferably in an amount of 30% or less of the heavy aromatic feed. The heavy aromatic feed stream preferably comprises at least about 90 mass % aromatics, and may be derived from the same or different known refinery and petrochemical processes as the benzene/toluene feed stream and/or may be recycled from the separation of the transalkylation effluent.

The feed to the transalkylation zone also comprises an olefin. As used herein, the term "olefin" includes alkenes, cyclic alkenes, alkenylbenzenes and other bromine reactive species as determined by UOP304. The olefin content of the feedstock and other streams herein is reported as a Bromine Index, which is a commonly used indicator of the olefin content. The feed according to the invention has a Bromine Index of more than 50. In an embodiment, the feed has a Bromine Index of at least about 100, the feed may have a Bromine Index of more than 600. In an exemplary embodiment, the feed has a Bromine Index of at least about 1000, and the feed may have a Bromine Index of at least about 2000. The Bromine Index is determined in accordance with UOP Method 304, obtainable through ASTM International, 100 Barr Harbor Drive, West Conshohocken, Pa., USA. It should be pointed out that there are other standard test methods for Bromine Index. However, these methods do not necessarily provide the same results as UOP304. Therefore, it is to be understood that the numerical values of Bromine Index herein are as measured by UOP304 only and are reported in units of milligrams of bromine per 100 g of sample.

When multiple feed streams are introduced to the transalkylation zone, overall or total feed properties such as the above Bromine Index values of the feed are the weighted average Bromine Index of all the feed streams introduced. The aromatic feed to a transalkylation reaction zone is usually first heated by indirect heat exchange against the reaction product stream and then is heated to reaction temperature by exchange with a warmer stream, steam or a furnace. The feed is preferably transalkylated in the vapor phase and in the presence of hydrogen. In an embodiment a hydrogen stream is introduced to the transalkylation zone. The hydrogen stream may comprise other compounds, e.g. $C_1$ to $C_4$ hydrocarbons, in addition to hydrogen. Hydrogen and hydrocarbons may be recycled in the process as described below. If present, free hydrogen is associated with the feedstock and recycled hydrocarbons, if any, in an amount from about 0.1 moles per mole of aromatics up to 10 moles per mole of aromatics. This ratio of hydrogen to aromatics is also referred to as hydrogen to hydrocarbon ratio.

The feed is then passed through one or more reactors containing the transalkylation catalyst to produce a reaction product stream comprising unconverted feed and product hydrocarbons including xylenes. The reaction product stream has a greater amount of xylenes relative to the feed stream on a mass basis, and a reduced amount of olefins relative to the feed as determined by Bromine Index. Benzene may also be produced. This reaction product stream is normally cooled by indirect heat exchange against the aromatic feed stream entering the transalkylation zone and may be further cooled through the use of air or cooling water. The reaction product stream may be separated e.g. in a vapor-liquid separator to produce a vapor phase hydrogen stream and a liquid phase reaction product stream. The vapor phase hydrogen stream includes hydrogen and light hydrocarbons which may be recycled and combined with the feed as described above. The liquid phase reaction product stream may be passed into a stripping column in which substantially all $C_5$ and lighter hydrocarbons present are concentrated into an overhead stream and removed from the process. As used herein, the term "substantially all" means an amount generally of at least 90%, preferably at least 95%, and optimally at least 99%, by weight, of a compound or class of compounds in a stream. The stripping column also produces a net stripper bottoms stream, which is referred to herein as the transalkylation zone effluent.

The transalkylation zone effluent may be further separated in a distillation zone comprising at least one distillation column to produce a benzene product stream. Various flow schemes and combinations of distillation columns to separate transalkylation zone effluent via fractional distillation are well known in the art. In addition to the benzene product stream, the distillation zone may produce a toluene product stream, and a $C_8+$ product stream. See, e.g., U.S. Pat. No. 7,605,295. It is also known that the transalkylation zone stripper column may be designed and operated to produce a benzene product stream. See, e.g., U.S. Pat. No. 6,740,788. Thus, the reaction product stream contains a benzene fraction that may be separated by fractional distillation to produce a benzene product stream.

In another embodiment, the transalkylation effluent is separated into a light recycle stream, a mixed $C_8$ aromatics product, and a heavy aromatic product stream in a distillation zone. The mixed $C_8$ aromatic product may be sent for recovery of para-xylene and/or other isomers. The light recycle stream may be diverted to other uses such as benzene and toluene recovery, but may be recycled, in part, to the transalkylation zone. The heavy recycle stream contains substantially all of the C₉ and heavier aromatics and may be partially or totally recycled to the transalkylation reaction zone.

In an embodiment, the transalkylation conditions are sufficient to provide a reaction product stream having a higher concentration of xylenes than the transalkylation feed and an olefin content that is at least 60% lower than the olefin content of the feed as determined by Bromine Index. In an embodiment, the olefin content of the product is at least 80% lower than the olefin content of the feed as determined by Bromine Index, and may be at least 90% lower, preferably at least 95% lower than the olefin content of the feed as determined by Bromine Index.

Contacting the feed with the catalyst can be effected in any conventional or otherwise convenient manner and may occur as a batch or continuous type of operation. In an embodiment, the catalyst is disposed in one or more fixed beds in a reaction zone of a vertical reactor with the aromatic feed charged through the bed in an upflow or downflow manner. Transalkylation conditions may include a temperature in a range of from about 200° C. to about 540° C., preferably between about 200° C. to about 480° C.; a pressure in a range of from about 100 kPa to about 6 MPa absolute; and a weight hourly space velocity (WHSV, i.e., weight of aromatic feed introduced per weight of catalyst per hour) in a range of from about 0.1 to about 20 hr⁻¹, preferably ranging from about 1 to about 10 hr⁻¹.

The transalkylation conditions include the presence of a transalkylation catalyst comprising: an aluminosilicate zeolite having an MOR framework type, an MFI molecular sieve having a Si/Al2 molar ratio of less than 80, a metal component, and an inorganic oxide binder.

Aluminosilicate zeolite having an MOR framework is described in ATLAS OF ZEOLITE FRAMEWORK TYPES, 6th Revised Edition, C. H. Baerlocher, L. B. McCusker, and D. H. Olson, editors, Elsevier (2007), pp. 218-219. The MOR framework comprises four- and five-membered rings of SiO₄ and AlO₄ tetrahedra to form a crystal lattice comprising 12-ring channels running parallel along a crystal axis to give a tubular configuration. In an embodiment, the aluminosilicate zeolite having an MOR framework comprises mordenite. Where mordenite is a component of the catalyst, the mordenite preferably has a Si/Al₂ molar ratio of less than about 40. The Si/Al₂ molar ratio of mordenite in an embodiment is less than about 25, and in another embodiment the mordenite Si/Al₂ molar ratio is between about 15 and about 25. Mordenite may be synthesized with a Si/Al₂ molar ratio of between about 10 and about 20. Mordenite is preferably at least partially in the hydrogen form and/or may be dealuminated by a variety of techniques, e.g. steaming, and acid extraction of aluminum to increase the Si/Al₂ ratio of the mordenite.

In another embodiment, the aluminosilicate zeolite having an MOR framework comprises UZM-14. UZM-14 is described in U.S. Pat. No. 7,687,423, which is incorporated herein by reference in its entirety. UZM-14 comprises globular aggregates of crystallites having a MOR framework type comprising 12-ring channels, and one or more of the following distinctive characteristics: a mesopore volume of at least about 0.10 cc/gram, preferably at least about 0.13 cc/gram, more preferably at least about 0.2 cc/gram; a mean crystallite length parallel to the direction of the 12-ring channels of about 60 nm or less, preferably about 50 nm or less; a Si/Al₂ mole ratio of between about 8 and about 50, and preferably is no more than about 30; and at least about 1×10¹⁹ 12-ring channel openings per gram of UZM-14 material.

In an embodiment, UZM-14 comprises globular aggregates of crystallites having a MOR framework type comprising 12-ring channels, a silica-alumina mole ratio of from about 8 to no more than about 30, a mesopore volume of at least about 0.10 cc/gram, and a mean crystallite length parallel to the direction of the 12-ring channels of about 60 nm or less.

UZM-14 has an empirical composition in the as-synthesized form on an anhydrous basis expressed by the empirical formula:

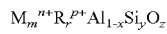

$$M_m^{n+}R_r^{p+}Al_{1-x}Si_yO_z$$

where M is at least one exchangeable cation and is selected from the group consisting of alkali and alkaline earth metals including but not limited to lithium, sodium, potassium, rubidium, cesium, calcium, strontium, barium and mixtures thereof. R is at least one organic cation selected from the group consisting of protonated amines, protonated diamines, quaternary ammonium ions, diquaternary ammonium ions, protonated alkanolamines, and quaternized alkanolammonium ions. Relating the components, "m" is the mole ratio of M to Al and varies from about 0.05 to about 0.95; "r" is the mole ratio of R to Al and has a value of about 0.05 to about 0.95; "n" is the weighted average valence of M and has a value of about 1 to about 2; "p" is the weighted average valence of R and has a value of about 1 to about 2; "y" is the mole ratio of Si to Al and varies from about 3 to about 50; and "z" is the mole ratio of O to Al and has a value determined by the equation: $z=(m \cdot n + r \cdot p + 3 + 4y)/2$.

The catalyst also includes an MFI molecular sieve having a Si/Al₂ molar ratio of less than 80. Zeolites having an MFI type framework are described in ATLAS OF ZEOLITE FRAMEWORK TYPES, 6th Revised Edition, C. H. Baerlocher, L. B. McCusker, and D. H. Olson, editors, Elsevier (2007). MFI type zeolites have a 3-dimensional 10-ring channel system: [100] 10-MR 5.1×5.5 Å and [010] 10-MR 5.3×5.6 Å. In an embodiment, MFI molecular sieves used in the catalysts of this invention have a Si/Al₂ molar ratio of less than about 40, preferably less than about 25, for example, between about 15 to about 25. An example of a suitable MFI molecular sieve for inclusion in the catalyst includes, but is not limited to, ZSM-5, which is disclosed in U.S. Pat. No. 3,702,886, incorporated herein, by reference thereto. Suitable MFI molecular sieves are also available, for example, from Zeolyst International of Conschocken, Pa. and Tosoh Corporation of Tokyo, Japan.

In an embodiment, the MFI molecular sieve has a "Total Acidity" of at least about 0.15, preferably at least about 0.25, and more preferably at least about 0.4, for example, 0.4 to 0.8. Total Acidity is determined by Ammonia Temperature Programmed Desorption (Ammonia TPD). The Total Acidity of the MFI molecular sieve may be that of the MFI to be used in making the catalyst of the invention or may be achieved during the preparation of the catalyst. Typically, the MFI molecular sieve is at least partially in the hydrogen form in the finished catalyst. The Ammonia TPD process involves first heating a sample (about 250 milligrams) of molecular sieve at a rate of about 5° C. per minute to a temperature of about 550° C. in the presence of a 20 volume percent oxygen in helium atmosphere (flow rate of about 100 milliliters per minute). After a hold of about one hour, helium is used to flush the system (about 15 minutes) and the sample is cooled to about 150° C. The sample is then saturated with pulses of ammonia in helium at about 40 milliliters per minute. The total amount of ammonia used is greatly in excess of the amount required to saturate all the acid sites on the sample. The sample is purged with helium (about 40 milliliters per minute) for about 8 hours to remove physically adsorbed ammonia. With the helium purge continuing, the temperature is increased at a rate of about 10° C. per minute to a final temperature of 600° C. The amount of ammonia desorbed is monitored using a calibrated thermal conductivity detector. The total amount of ammonia is found by integration. Dividing the total amount of ammonia by the dry weight of the sample yields the Total Acidity. As used herein, values of Total Acidity are given in units of millimoles of ammonia per gram of dry sample.

The inorganic oxide binder of the catalyst comprises such materials as alumina, silica, zirconia, titania, thoria, boria, magnesia, chromia, stannic oxide, and the like as well as combinations and composites thereof, for example silica-alumina, alumina-zirconia, alumina-titania, aluminum phosphate, and the like. Alumina is a preferred refractory inorganic oxide binder. As is well known in the art, a precursor of the desired refractory inorganic oxide may be used to form, bind, and/or otherwise prepare the catalyst. Such binder precursors or sources may be converted into a refractory inorganic oxide binder, e.g. by calcination. The alumina may be any of the various aluminum oxides, hydroxides, and gels, including boehmite, pseudo-boehmite, gibbsite, bayerite, and the like, especially transition and gamma aluminas Suitable aluminas are commercially available, e.g. under the trade names CATAPAL B and VERSAL 250.

In an embodiment, the metal component of the catalyst comprises a metal consisting essentially of molybdenum. In another embodiment, the metal component comprises molybdenum. In an embodiment, the molybdenum content of the catalyst ranges from about 0.5 wt % to about 10.0 wt % as the metal based upon the total weight of the catalyst. In another embodiment, the molybdenum content of the catalyst ranges from about 1 wt % to about 8 wt %, and may range from about 2 wt % to about 7 wt % as the metal based upon the total weight of the catalyst.

The metal component may be incorporated into the catalyst in any suitable manner such as comulling, coprecipitation or cogellation with the carrier material, ion exchange, or impregnation. The metal component may exist within the final catalyst as a compound such as an oxide, sulfide, halide, or oxyhalide, in chemical combination with one or more of the other ingredients of the composite, or as an elemental metal. One method of preparing the catalyst involves the use of a water-soluble or solvent-soluble, decomposable compound of the metal to impregnate the molecular sieve-containing support. Alternatively, a metal compound may be added at the time of compositing the molecular sieve component and binder.

The weight ratio of the MFI molecular sieve component to the aluminosilicate zeolite having the MOR framework may range from about 1:10 to 5:1, preferably from about 1:10 to 2:1. In an embodiment, the aluminosilicate zeolite component having the MOR framework comprises from about 20 wt % to about 80 wt % of the catalyst, the MFI molecular sieve component comprises from about 10 wt % to about 70 wt % of the catalyst, and the inorganic oxide binder comprises between about 1 wt % and about 40 wt % of the catalyst.

The catalyst may optionally include an additional molecular sieve component preferably selected from one or more of MEL, EUO, FER, MFS, MTT, MTW, MWW, MAZ, TON and FAU (IUPAC Commission on Zeolite Nomenclature) and UZM-8 (see U.S. Pat. No. 6,756,030 which is herein incorporated by reference in its entirety). The catalyst may optionally include a fluoride component in an amount ranging from about 0.1 wt % to about 5.0 wt % of fluoride based upon the total weight of the catalyst. The fluoride component may be incorporated into the catalyst by any known technique, e.g. impregnation.

The techniques used to prepare the catalyst are well known to those of ordinary skill in the art. The catalyst can be formed by combining the aluminosilicate zeolite component having the MOR framework, the MFI molecular sieve component, and the inorganic oxide binder and/or a precursor thereof in any conventional or otherwise convenient manner to form spheres, pills, pellets, granules, extrudates, or other suitable particle shapes. For example, finely divided aluminosilicate zeolite having the MOR framework and MFI molecular sieve particles, and metal salt particles can be dispersed in an alumina sol, and the mixture in turn dispersed as droplets in a hot oil bath whereby gelation occurs with the formation of spheroidal gel particles. A preferred method comprises mixing a finely divided form of the selected aluminosilicate zeolite having the MOR framework, MFI molecular sieve particles, a binder and/or precursor thereof, with a metal salt and, optionally, a lubricant; and compressing the mixture into pills or pellets. Alternatively, and still more preferably, the aluminosilicate zeolite having the MOR framework, MFI molecular sieve particles, binder and/or precursor thereof, and metal salt are combined and admixed with a peptizing agent in a mixer-muller, a dilute nitric acid being one example of the suitable peptizing agent. The resulting dough can be pressured through a die or orifice of predetermined size to form extrudate particles which can be dried and calcined and utilized as such. A multitude of different extrudate shapes are possible, including, but not limited to, cylinders, cloverleaf, dumbbell and symmetrical and asymmetrical polylobes, with a trilobe form being favored. The extrudates also may be formed into spheres by means of a spinning disc or drum. The variously formed particles are then usually dried and/or calcined.

If the metal component is not included in the above forming steps, the formed particles produced above can be impregnated with a soluble, decomposable compound containing the metal component to form a composite. For example, typical compounds which may be employed include ammonium heptamolybdate, alkali metal molybdates (also peroxo-, di-, tri-, tetra-, hepta-, octa-, or tetradecamolybdate), molybdic acid, phosphomolybdic acid, Mo—P heteropolyanion compounds, acetyl acetonates, Mo(0) metal, Mo oxides, Mo peroxo complexes, and mixtures thereof. The composite is preferably calcined in an air atmosphere at a temperature of from about 425° C. to about 750° C., preferably at a temperature of from about 475° C. to about 600° C., over a period of from about 0.5 to about 10 hours. Typically, the formed particles are also calcined at similar conditions prior to the impregnation step. The catalyst preparation may include various optional steps such as drying and steaming which are well known in the art.

EXAMPLE 1

A catalyst was prepared by blending of UZM-14, MFI zeolite, and Catapal C to obtain a 50% UZM-14, 25% MFI zeolite, and 25% Catapal C mixture on a volatile free (VF) weight basis. The mixture also included a solution of ammonium heptamolybdate to obtain 5 wt % molybdenum (VF) in the final catalyst, and a solution of diluted nitric acid as the peptizing agent to form a dough. The dough was extruded as a cylinder and the catalyst was calcined at 580° C. for 20 minutes with 7.5% added steam. The UZM-14 zeolite used in this example was prepared according to Example 1 of U.S. Pat. No. 7,687,423 except the crystallization temperature was 140° C. and commercial scale equipment was used. After synthesis, the UZM-14 material was washed, exchanged with an ammonium sulfate solution and dried. This material had the following properties: a molar $SiO_2/Al_2O_3$ ratio of 18.0, a BET surface area of 440 $m^2/g$, a micropore volume of 0.20 cc/gram, and a mesopore volume of 0.22 cc/gram. The MFI zeolite was CBV 2314, a ZSM-5 material with $SiO_2/Al_2O_3$ of 23, obtained from Zeolyst International. Catapal C was purchased from Vista Chemical Company. The finished catalyst had a BET surface area of 360 m$^2$/g and a total pore volume of 0.50 cc/g. The piece density was 1.200 g/cc. Corrected

EXAMPLE 2

The catalyst prepared in example 1 was tested in an aromatics transalkylation test with a feed blend of 50 wt % toluene and 50 wt % a xylene column bottoms stream, i.e. C$_9$+ aromatics. The feed had nominally the composition in weight percent given in Table 1. Prior to testing, the catalyst was sulfided in-situ as is well known in the art to convert the MoO$_3$ and/or molybdenum metal of the calcined catalyst, at least partially, to molybdenum sulfide. An objective of catalyst sulfiding is to add a fixed amount of sulfur to the catalyst. This was accomplished by passing excess dimethyl disulfide (DMDS), equivalent to 250 ppm-wt as sulfur in the feed over the catalyst at a temperature ranging from about 280° C. to 360° C., a pressure of 2,758 kPa(g), a weight hourly space velocity of 4, and a hydrogen to hydrocarbon ratio of 2 for 30 hours. This procedure provides a sulfided catalyst with a relatively fixed sulfur content such that longer sulfiding with excess DMDS will not increase the sulfur content of the catalyst further. After the sulfiding procedure was complete, feed without DMDS was introduced to the catalyst and testing conditions of a pressure of 2,758 kPa(g), a weight hourly space velocity of 4, and a hydrogen to hydrocarbon ratio of 2 were established. The reactor temperature was adjusted to obtain 50% overall conversion, calculated as the net disappearance of toluene, C$_9$ and C$_{10}$ aromatics from the feed stream, i.e. (mass of toluene, C$_9$ and C$_{10}$ aromatics in the feed minus mass of toluene, C$_9$ and C$_{10}$ aromatics in the reaction product)/mass of toluene, C$_9$ and C$_{10}$ aromatics in the feed, on a weight percent basis.

After reaching steady-state at test conditions, two C$_9$ olefins were added to the feed to determine olefin removal during transalkylation. The modified feed contained 0.42 wt % alpha-methylstyrene and 0.35 wt % indene. The Bromine Index of the modified feed was determined to be 1,067. The liquid product from the transalkylation reactor was analyzed by GC and no alpha-methylstyrene or indene was detected, indicating complete conversion of the olefins. The Bromine Index of the liquid product was determined to be 21. These results demonstrate excellent olefin removal capability of a transalkylation catalyst containing molybdenum as exemplified by example 1.

TABLE 1

| | |
|---|---|
| Toluene | 50 |
| Propylbenzene | 2.1 |
| Methylethylbenzene | 10.5 |
| Trimethylbenzene | 24.5 |
| Indane | 0.7 |
| Methylpropylbenzene | 1.8 |
| Diethylbenzene | 0.5 |
| Dimethylethylbenzene | 3.5 |
| Tetramethylbenzene | 2.1 |
| Other C$_{10}$ aromatics | 1.6 |
| C$_{11}$+ aromatics | 2.7 |

The invention claimed is:

1. A process for transalkylating aromatic hydrocarbons and removing olefins from a feed having a Bromine Index of more than 50, the process comprising: introducing a feed comprising the olefin and aromatic hydrocarbon compounds comprising at least one of toluene and C9+ aromatics to a transalkylation zone; contacting the feed with a transalkylation catalyst in the transalkylation zone under transalkylation conditions; and producing a reaction product stream having an increased concentration of xylenes relative to the feed and at least 60% lower olefins as determined by Bromine Index relative to the feed; wherein the catalyst comprises an aluminosilicate zeolite component having an MOR framework type, an MFI molecular sieve component having a Si/Al$_2$ molar ratio of less than 80, an inorganic oxide binder, and a metal component comprising a metal consisting essentially of molybdenum.

2. The process of claim 1 wherein the feed has a Bromine Index of more than 600.

3. The process of claim 1 wherein the olefin content of the reaction product stream is at least 80% lower than the olefin content of the feed as determined by Bromine Index.

4. The process of claim 1 wherein the olefin content of the reaction product stream is at least 90% lower than the olefin content of the feed as determined by Bromine Index.

5. The process of claim 1 wherein the feed has a Bromine Index of at least about 1000.

6. The process of claim 5 wherein the olefin content of the reaction product stream is at least 80% lower than the olefin content of the feed as determined by Bromine Index.

7. The process of claim 6 wherein the process has an overall conversion of at least about 50%, the overall conversion calculated as (the mass of toluene, C$_9$ and C$_{10}$ aromatics in the feed minus the mass of toluene, C$_9$ and C$_{10}$ aromatics in the reaction product)/the mass of toluene, C$_9$ and C$_{10}$ aromatics in the feed, on a weight percent basis.

8. The process of claim 1 wherein the transalkylation conditions include a temperature ranging from about 200° C. to about 480° C.

9. The process of claim 8 wherein the transalkylation conditions further include a pressure ranging from about 100 kPa to about 6 MPa absolute; and a weight hourly space velocity ranging from about 1 to about 10 hr$^{-1}$.

10. The process of claim 1 wherein the inorganic oxide binder comprises a material selected from the group consisting of alumina, silica, zirconia, titania, thoria, boria, magnesia, chromia, stannic oxide, and combinations thereof.

11. The process of claim 1 wherein the inorganic oxide binder comprises alumina.

12. The process of claim 1 wherein the aluminosilicate zeolite comprises mordenite.

13. The process of claim 1 wherein the aluminosilicate zeolite comprises UZM-14.

14. The process of claim 1 wherein the MFI molecular sieve comprises ZSM-5.

15. The process of claim 1 wherein the catalyst has a molybdenum content ranging from about 0.5 wt % to about 10.0 wt % as the metal based upon the total weight of the catalyst.

16. The process of claim 1 wherein the catalyst has a molybdenum content ranging from about 1 wt % to about 8 wt % as the metal based upon the total weight of the catalyst.

17. The process of claim 1 wherein the metal is molybdenum.

18. The process of claim 1 wherein the metal component comprises molybdenum sulfide.

19. The process of claim 1 wherein the process has an overall conversion of at least about 50%, the overall conversion calculated as (the mass of toluene, C$_9$ and C$_{10}$ aromatics in the feed minus the mass of toluene, C$_9$ and C$_{10}$ aromatics in the reaction product)/the mass of toluene, C$_9$ and C$_{10}$ aromatics in the feed, on a weight percent basis.

* * * * *